United States Patent
Moktali et al.

(10) Patent No.: US 12,102,295 B2
(45) Date of Patent: *Oct. 1, 2024

(54) DIGITAL DEVICE FACILITATING BODY CAVITY SCREENING AND DIAGNOSIS

(71) Applicants: Periwinkle Technologies Pvt. Ltd., Pune (IN); Veena Moktali, Maharashtra (IN); Koustubh Naik, Maharashtra (IN)

(72) Inventors: Veena Moktali, Maharashtra (IN); Koustubh Naik, Baner Pune (IN)

(73) Assignees: Periwinkle Technologies Pvt. Ltd., Pune (IN); Veena Moktali, Pune (IN); Koustubh Naik, Pune (IN)

(*) Notice: Subject to any disclaimer, the term of this patent is extended or adjusted under 35 U.S.C. 154(b) by 961 days.

This patent is subject to a terminal disclaimer.

(21) Appl. No.: 16/648,257

(22) PCT Filed: Dec. 1, 2017

(86) PCT No.: PCT/IB2017/057562
§ 371 (c)(1),
(2) Date: Mar. 18, 2020

(87) PCT Pub. No.: WO2019/053499
PCT Pub. Date: Mar. 21, 2019

(65) Prior Publication Data
US 2020/0237200 A1     Jul. 30, 2020

(30) Foreign Application Priority Data
Sep. 18, 2017   (IN) .............................. 201721032933

(51) Int. Cl.
*A61B 1/015*    (2006.01)
*A61B 1/00*     (2006.01)
(Continued)

(52) U.S. Cl.
CPC .......... *A61B 1/015* (2013.01); *A61B 1/00016* (2013.01); *A61B 1/00097* (2022.02);
(Continued)

(58) Field of Classification Search
CPC ............ A61B 1/00082; A61B 1/00096; A61B 1/00103; A61B 1/00119; A61B 1/00135;
(Continued)

(56) References Cited

U.S. PATENT DOCUMENTS

2003/0032863 A1*  2/2003  Kazakevich ....... A61B 1/00105
                                                         600/173
2005/0065543 A1*  3/2005  Kahle ................... A61B 90/92
                                                         606/190
(Continued)

FOREIGN PATENT DOCUMENTS

WO     2017154005 A1    9/2017

*Primary Examiner* — Aaron B Fairchild
*Assistant Examiner* — Stephen Floyd London

(57) ABSTRACT

A digital device (100) facilitates body cavity diagnosis without using a speculum. The device (100) comprises a casing (101) for enclosing a probe with additional channels (102). The additional channels (102) comprises a plurality of instruments. The probe (103) is configured for optical and digital diagnosis of abnormalities in the body cavities. The probe (103) is connected to wireless communication components for displaying captured images. The probe (103) in association with angulation wires (107) facilitates capturing the images of abnormalities along with digital image diagnosis, wherein the angulation wires (107) provides maximum field of surround-vision. The casing (101) has a transparent cap (105) configured for visualizing structure of the cavity. The casing (101) comprises an expandable outer cuff (104), for separating the walls of a body part.

14 Claims, 3 Drawing Sheets

(51) Int. Cl.
*A61B 1/005* (2006.01)
*A61B 1/04* (2006.01)
*A61B 1/05* (2006.01)
*A61B 1/055* (2006.01)
*A61B 1/303* (2006.01)
*A61B 5/00* (2006.01)
*A61B 10/02* (2006.01)
*A61K 49/00* (2006.01)

(52) U.S. Cl.
CPC ...... *A61B 1/00137* (2013.01); *A61B 1/00142* (2013.01); *A61B 1/00193* (2013.01); *A61B 1/0057* (2013.01); *A61B 1/043* (2013.01); *A61B 1/05* (2013.01); *A61B 1/055* (2013.01); *A61B 1/303* (2013.01); *A61B 5/0084* (2013.01); *A61B 5/4337* (2013.01); *A61B 5/7264* (2013.01); *A61B 10/02* (2013.01); *A61K 49/006* (2013.01); *A61B 1/00009* (2013.01); *A61B 2010/0216* (2013.01)

(58) Field of Classification Search
CPC ... A61B 1/00137; A61B 1/012; A61B 1/0125; A61B 1/015; A61B 1/018; A61B 1/00016; A61B 1/00091; A61B 1/00094; A61B 1/00181; A61B 1/00183; A61B 1/00193; A61B 1/00194; A61B 1/043; A61B 2017/3456; A61B 2017/3486; A61B 10/04; A61M 2025/015; A61M 16/0436; A61M 16/0438; A61M 25/10182

USPC ........................................................ 606/192
See application file for complete search history.

(56) References Cited

U.S. PATENT DOCUMENTS

| | | | |
|---|---|---|---|
| 2006/0276692 A1* | 12/2006 | Kucklick | A61B 1/317 600/175 |
| 2007/0142706 A1* | 6/2007 | Matsui | A61B 1/00154 600/114 |
| 2009/0023996 A1* | 1/2009 | Fujikura | A61M 25/10188 600/115 |
| 2010/0010298 A1* | 1/2010 | Bakos | A61B 1/015 600/114 |
| 2011/0251458 A1* | 10/2011 | Terliuc | A61B 1/00082 600/116 |
| 2012/0157767 A1* | 6/2012 | Jendoubi | G16H 30/20 600/109 |
| 2013/0281781 A1* | 10/2013 | Farhadi | A61B 1/00148 600/116 |
| 2014/0378957 A1* | 12/2014 | Orphanos | A61B 18/1482 606/171 |
| 2015/0216403 A1* | 8/2015 | Whitmore, III | A61B 1/307 600/103 |
| 2015/0313633 A1* | 11/2015 | Gross | A61B 1/00087 606/185 |
| 2017/0020627 A1* | 1/2017 | Tesar | A61B 90/361 |
| 2017/0258392 A1 | 9/2017 | Skieller et al. | |

* cited by examiner

DIGITAL DEVICE FACILITATING BODY CAVITY SCREENING AND DIAGNOSIS

CROSS-REFERENCE TO RELATED APPLICATIONS AND PRIORITY

The present application does claim priority from Indian Patent Application 201721032933 dated Sep. 18, 2017 and PCT Application PCT/IB2017/057562 dated Dec. 1, 2017.

TECHNICAL FIELD

The present subject matter described herein, in general, relates to a field of visual inspection of body cavities for screening abnormalities. In particular, the present subject matter is related to a digital device facilitating body cavity screening and diagnosis.

BACKGROUND

Body cavities are visually inspected or diagnosed using endoscopes just as orifices are visually inspected using either specialized types of endoscopes or external scopes (cameras). The characteristics of the scope such as size, power, flexibility, optics and light used, camera technology used, any additional sensors used, typically depend on the organ being inspected and the purpose of the inspection. Visual Inspection for some specific organs and some specific purposes may also be supported by other procedures such as cleaning with swabs, scraping and brushing to collect sample, site preparation to demarcate patterns etc. Result of a Visual Inspection depends heavily on the clarity of the images/videos captured and the inspector's skill level. Consequently, these results are very subjective.

Even if the diagnosis technique used may be highly sensitive but is not specific enough, thereby burden on diagnostic facilities increases. As a consequence, total spend on diagnosis in terms of effort and money is typically high, both by the healthcare system and the patient. Therefore, it is often the aim of experts in this area to evaluate and recommend a screening technique which may be cost effective, highly sensitive, and highly specific. This becomes even more relevant for low resource settings where availability of screening facilities, diagnostic facilities, and trained healthcare providers is an issue that may impact the patient experience and outcome directly.

For example, in case of cervical cancer, acetic acid application may he performed for opening the cervical region using an instrument called speculum. In such a case of cervical cancer the screening camera may need high power lenses and illumination for visual inspection from a distance. Further, dependency on electricity increases, specialized training is required to operate and maintain the camera, discomfort is caused due to the speculum and is expensive. Therefore, an affordable trans-vaginal scope is needed which can be used without a speculum preferably to provide a surround-view that can be captured on a computing device so that the data may be put through a machine learning system to provide a guidance to the healthcare providers responsible for screening. The system that is connected to this data should be able to link a follow-up care regime for a true positive patient appropriate to the type(s) of abnormalities that were detected.

Therefore, there is a long-standing need of a digital device facilitating body cavity screening and diagnosis which has smaller lenses, smaller in size, can be operated easily with the help of semiskilled personnel, provides comfort to the patient during screening or diagnosis, cost effective, electricity independent, speculum free and can be connected to specialized software.

SUMMARY

This summary is provided to introduce concepts related to a digital device facilitating body cavity screening and diagnosis. This summary is not intended to identify essential features of the claimed subject matter nor is it intended for use in determining or limiting the scope of the claimed subject matter.

In one implementation, a digital device facilitating body cavity screening and diagnosis is illustrated in accordance to the present subject matter. The digital device is characterized in enabling the body cavity diagnosis without using a speculum. The digital device may comprise a casing for enclosing a probe with additional channels. The additional channels may comprise of a plurality of instruments. The probe may be configured for optical and digital screening and diagnosis of abnormalities in the body cavities. The probe may be capable of being connected to local and wireless remote communication components for displaying one or more captured images. The probe may comprise of an in-situ image capturing means with a light source for capturing images of the abnormalities. The probe may further comprise image processing means coupled to a computing device for digital image diagnosis. The probe may further comprise one or more angulation wires for providing angulation control to the image capturing means. The casing may comprise a transparent cap along with a hole that aligns with the additional channel of the casing, wherein the transparent cap may be configured for visualizing walls and structure of the cavity. The casing may further comprise an expandable outer cuff on the exterior of said casing, for separating the walls of a body part. The casing may be rigid or flexible, and the probe may be capable of separating from the casing.

In another implementation, a method facilitating body cavity screening and diagnosis is illustrated in accordance with the present subject matter. The method may be characterized in enabling the body cavity diagnosis without using a speculum. The method may comprise introducing, a digital device for body cavity diagnosis in required body cavity for diagnosis of abnormalities. The method may further comprise applying, via a spray, of a liquid agent on the body cavity for diagnosing of abnormalities. The method may furthermore comprise capturing, via image capturing means the images of the abnormalities. The method may comprise processing via image processing means, the images for annotation and decision making. The method may comprise displaying, via wireless remote communication components, the processed results from the image processing means.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

The present invention relates to a digital device facilitating visual inspection or diagnosis of body cavities and/or orifices. When said device may be inserted into the body cavity, the device may have capabilities to:

(a) open the body cavity walls gently with a pressure cuff (b) provide a maximum field of surround-vision with a miniature camera equipped with a light source perhaps having various colors of lights and an optional angulation mechanism (c) provide access to the body cavity through a working channel (d) allow application of chemicals to the abnormalities in the body cavity in order to help demarcation of patterns or enhance the appearance—an example being spraying of acetic acid to cause whitening of precancerous tissue (e) capture images and videos using controls on the camera tube or a mobile phone or PC or any suitable computing device connected to the camera either with its data cable or over any suitable communication protocol (f) capture human-input data through said computing device and associate it to the images to make it a complete record (g) and on demand, analyze the images and videos captured and the tagged data (combination henceforth referred to as a "record") through use of a computer implemented platform perhaps residing on the same computing device or on any other computing device which can access said "record", which performs digital image processing and interpretation with use of artificial intelligence algorithms to indicate abnormalities detected and their nature, to provide a preliminary guidance for subsequent manual review.

Figure 1:
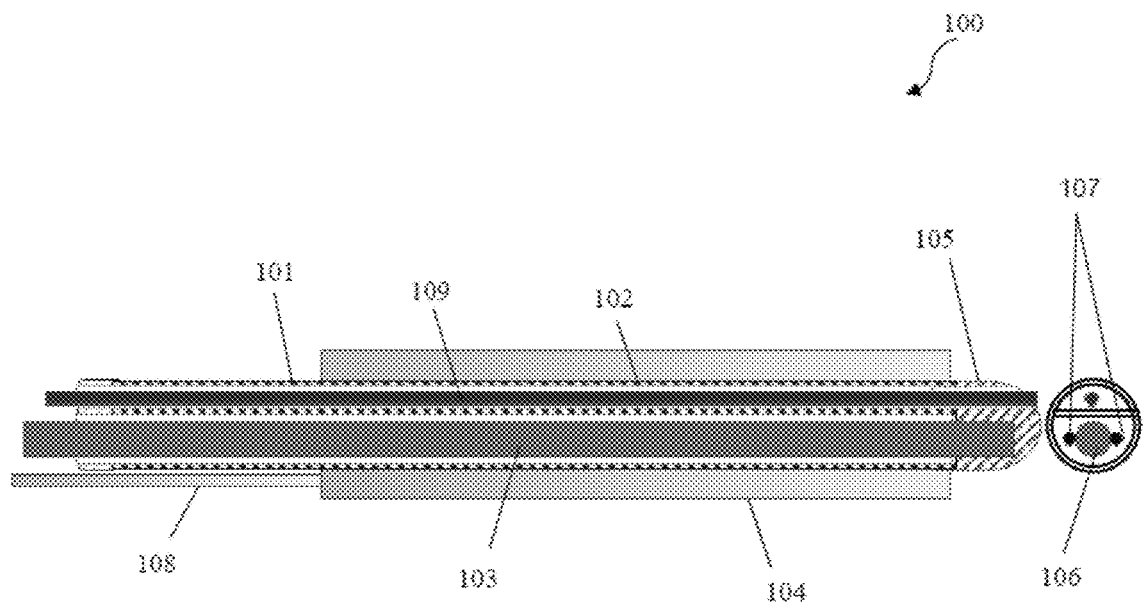
FIG. 1 illustrates, a 2-dimensional view 100 of the digital device 100 facilitating body cavity screening and diagnosis.

Referring now to FIG. 1, a digital device 100 facilitating body cavity screening and diagnosis is illustrated in accordance to the present subject matter. The present subject matter proposes a screening and diagnostic device that can fit into a body cavity. In one embodiment, the digital device 100 for body cavity diagnosis may comprise a casing 101, further comprising two compartments wherein one compartment comprises additional channels 102, and another compartment comprises a probe 103. The casing 101 further comprises an expandable outer cuff 104, transparent cap 105, and a tube 108. In one embodiment, the casing 101 may be configured for enclosing the probe 103 along with additional channels 102 wherein the additional channels comprise of a plurality of instruments. The probe 103 may comprise an in-situ image capturing means 106 with a light source for capturing images of the abnormalities, image processing means (not shown in figure) coupled to a computing device for digital image diagnosis and one or more angulation wires 107 for providing angulation control to the image capturing means 106. The probe 103 may be configured for optical and digital diagnosis of abnormalities in the body cavities, and wherein the probe 103 may be capable of being connected to local and wireless remote communication components for displaying one or more captured images. The casing 101 may comprise the transparent cap 105, with a hole that may be aligned with the additional channels 102 of the casing 101. The transparent cap 105 may be configured for visualizing walls and structure of the body cavity. The casing 101 may comprise the expandable outer cuff 104 on the exterior of the casing 101, wherein said outer cuff 104 may be configured for separating the walls of a body part wherein the body cavity is to be diagnosed. The casing 101 may be rigid or flexible and the probe 103 may be capable of separating from the casing 101. The digital device 100 for body cavity diagnosis, may be characterized in enabling the body cavity diagnosis without using a speculum.

The casing 101 may be sterilized having length 150 mm or more and outer diameter 20 mm or less. In one embodiment, the casing 101 may be made of a flexible stainless-steel hose of a biofriendly grade in order to help usage in openings of the body part such as but may not be limited to esophagus. In another embodiment, the casing 101 may be made of a suitable type of bio-friendly plastic. In yet another embodiment, the casing 101 may be made of either steel, rubber, or soft plastic, wherein stainless steel facilitates autoclaving and soft plastic facilitates disposability. Therefore, the casing 101 may be disposable or sterilisable or autoclavable. The additional channels 102 of casing 101 may comprise plurality of instruments comprising a tube straw 109 for carrying a liquid agent, a spatula for scraping of cells, a cytobrush to collect scraped cells, a swab for cleaning, forceps to lift the walls of the cavity, a grasping device, pair of scissors to remove tissues. In one embodiment, the straw or tube 109 may have a dedicated channel that may be separate from the channels of the instruments. The tube 109 may be used for introducing a spray wherein, the tube 109 may be attached to an external spray pump which may contain acetic acid or Lugol's iodine suitably prepares as per Visual Inspection with acetic acid standards or Visual Inspection with Lugol's iodine standards (VIA/VILI). A separate channel for said tube 109 may facilitate repeated action of chemical application without setting up the channel every time after usage of the device 100. In one embodiment, the tube 109 may be disposable. The tube 109 may comprise markings, wherein said tube 109 may be inserted in the channel 102 till a specified marking on the tube 109. The outer end of the tube 109 may be connected to a pressure-pump container or mist spray canister. The container or canister may be filled with the desired liquid agent such as 3% or appropriate acetic acid or Lugol's iodine. While visualizing the spray, the liquid agent may be sprayed or pumped into the body cavity. In one embodiment, the tube 109 may have a felt-tip or bud-tip at a distal end, enabling the liquid agent to be applied while rotating the probe 103 gently through partial circular motion about its axis. The expandable outer cuff 104 may be inflated and fitted on the outside the casing 101. In one embodiment, said cuff 104 may be removed and changed. Said cuff 104 may be in a deflated position when introduced into the body cavity. The outer cuff 104 may be connected to an air-pump outside the body cavity using a thin rubber tube 108. When positioned inside the cavity, air can be pumped to inflate the outer cuff 104 in order to have a better view obtained for the image capturing means 106. In one embodiment, the outer cuff 104 may be inflatable and comprise rubber or plastic cuff inflated with gas or polymer gel cuff injected with liquid agent. The probe 103 may be of diameter of maximum 15 mm. In one embodiment, the digital probe 103 may be capable of providing stereoscopic vision for visualization of abnormalities in the body cavities. In one embodiment, the image capturing means 106 may comprise, but may not be limited to, a camera or like devices. The casing 101 may have a transparent bubble (rounded) cavity-end that may provide a viewport for the image capturing means 106 while at the same time protecting said image capturing means 106 from exposure to any microbes. This may ensure that the image capturing means 106 may not have to be separately sterilized as that can affect the lens. The image capturing means 106 may be communicatively connected to a computing device (not shown in figure) such as, but may not be limited to, a mobile phone, personal computer, laptop or like devices for transferring the images and videos captured to the device 100 using a suitable data communication protocol. In one embodiment, the image capturing means 106 may be a specially designed flexi-tip CMOS or CCD-chip device with a lens diameter small enough to provide a clear image from 3 mm distance minimum from the area being viewed. In another embodiment, the image capturing means 106 may be a standard CMOS borescope or a CCD scope or a fiberscope or a rod-lens endoscope-like camera (used without any other sheath). A distal tip of the image capturing means 106 may be rigid or flexible. The rigid distal tip may fit with one or more foroblique mirror tips of angular fits such as, but may not be limited to, 30°, 60°, 75° etc, in order to achieve surround vision. A flexible distal tip may have angulation wires 107 to the tip. The image capturing means 106 may have specifications comprising minimum 2-5 megapixel resolution, lens diameter of 7.5 mm or less, resolution of 640*480 or higher. In one embodiment, the image capturing means 106 such as camera, may be a UV-light camera with sensors that provide fluorescence information to the connected computing device. In another embodiment, the image capturing means 106 may be a regular fiberscope. In yet another embodiment, the image capturing means 106 may be a conventional rigid endoscope with rod lens system, without its sheath. In yet another embodiment, the image capturing means 106 may be a CCD-chip camera. In various embodiment, the size of the image capturing means lens, its focal lengths, and even the chip size of CMOS or CCD may vary depending on image clarity, resolution, and size required.

In an embodiment, the image capturing means 106 may be an integral instead of replaceable part of a plastic casing 101 fitted with a fixed acrylic or polycarbonate viewport bubble, when made available as a personal use device. In one embodiment, the image capturing means 106 may be in-situ and may comprise a light source (not shown in figure). The specifications of the light source such as the number of LEDs, their positions and distribution, and colors may vary depending on the illumination, image clarity, and filter effects required for the task at hand. In one embodiment, the image capturing means 106, inside the casing 101 may have a flexible tip with angulation or articulation wires 107, adjacent to the said tip for pliability to achieve surround vision. In an embodiment, the angulation wires 107 may be controlled by a pulley or a chain-sprocket mechanism with stoppers to limit the articulation and external knob(s) to control the turning in required direction. The diameter of angulation wires may be maximum of 5 mm diameter. The angulation wires 107 are located on one side each of the image capturing means 106. In one embodiment, the instruments passed through the additional channels 102 may protrude out of the hole in the transparent cap 105. In one embodiment, the transparent cap 105 on the lens side of the probe 103 may have a rounded smooth shape to allow painless insertion of the device 100 into the body cavity. Said transparent cap 105 may be hollow on the inner side in order to allow movement of probe head encased within and has a hole that aligns with the working channel of the casing 101 in order to allow outlet for the instruments as well as sprays. The transparent cap 105 may be made of a clear, transparent polycarbonate or any material that can provide full transparency and has a non-reflective surface. The transparent cap 105 may be screw-fit onto the casing 101 with the help of threading for disposable use or with the help of industrial glue for permanent use in which case it will be of a material that does not degrade with contact of recommended sterilization chemicals suitable to kill the microbes in that particular infected body organ.

In one embodiment, the image capturing means 106 may be communicatively connected to computing devices such as computer or laptop or a mobile phone. The software that may enable operation of computing device may be connected to but may not be limited to cloud. In one embodiment, said connectivity may be done via a USB port. In one embodiment, the light source on the image capturing means 106 which may be an LED-ring, around the tip of the image capturing means 106, may get powered from the computing device. The light or specific LEDs may be turned on or off using one of the external switches located on the image capturing means 106, wherein said switches may be located on the length of the image capturing means 106 which may extend outside the body cavity after insertion. With the white light turned on, the image capturing means 106 may be inserted into the main chamber of the casing 101 till a specified depth gauged easily by markings on the scope of the image capturing means 106. Once the image capturing means 106 may be firmly placed in the casing 101, this assembled device 100 is ready for insertion in the body cavity. A lubricant jelly may or may not be applied on the outer cuff 104 and casing assembly, depending on the case of the patient and cavity. Said device 100 may now be placed into the mouth of the body cavity when the subject is in a comfortable position suitable to the type of task at hand. While visualizing the progress of the device 100 into the body cavity with the help of real-time video on the connected computing device, the device 100 may be gently guided to its desired position. Markings on the casing 101 may indicate the threshold depths of insertion (maximum and minimum), keeping in mind age of patient and the body cavity type. The outer cuff 104 may then be slowly inflated while watching the pressure on a pump dial, keeping said pressure within specified limits as per age of patient and cavity type, wherein the pump dial may be a standard mechanical pressure gauge. The dial pump is just a mechanical pressure gauge that sits between the hand pump and the pipe that pushes air into the cuff. Said inflation may push open the body cavity walls gently from within, creating a clear visual path to frontal area. Said inflation may be enabled by the tube 108. In one embodiment, the outer cuff 104 may be inflatable and comprises of rubber or plastic cuff inflated with gas or polymer gel powder-filled cuff injected with a liquid causing the polymer powder to bloat into a gel. Further, captured images and videos of the abnormalities found in the body cavities may be processed by the image processing means (not shown in figure), coupled to the computing device, wherein the image capturing means 106 may enable capturing images of the abnormalities. The computing device may provide user interfaces for inputting relevant data related to the patient under examination. Captured images, videos, and data may comprise of a "record". Said record may be stored on the computing device as per applicable security norms. The record may or may not be transferred to a remote system such as a cloud server over an available and acceptable network protocol, as per requirement. The record may be shared with a remote expert who may provide a diagnostic confirmation after reviewing the original record and the diagnostic guidance provided by the device 100. Said record may be processed by a computer implemented platform comprised in the computing device. In one embodiment, the record may be shared to the remote expert via local and wireless remote communication. The computing device may comprise a logic that enables linkage of relevant care plans and captured images and videos of body cavities captured by the image capturing means 106 of the device 100. In one embodiment, the local and wireless remote communication enables connectivity between a remote consultation and a machine learning algorithm of the computing device. The local and wireless remote communication components may comprise of either of mobile phone, computer or laptop, via USB, BLE or WiFi of like sources. The record may be available on the computing device connected to the image capturing means 106 and/or the remote server, depending on the embodiment. The record may be processed in 3 or 4 steps: 1) digital image processing is performed on it to extract some data, 2) testing of this data along with data from the original record is done against a trained machine learning algorithm to present guidance for further human review of the case, 3) the original record and the diagnostic guidance may or may not be shared with a remote expert for diagnostic confirmation, 4) patient is linked to a follow-up care program, if required. The data input and presentation may happen in a language familiar to the user of the probe, depending on the application settings made by the user and application version at the time of usage.

Figure 2:
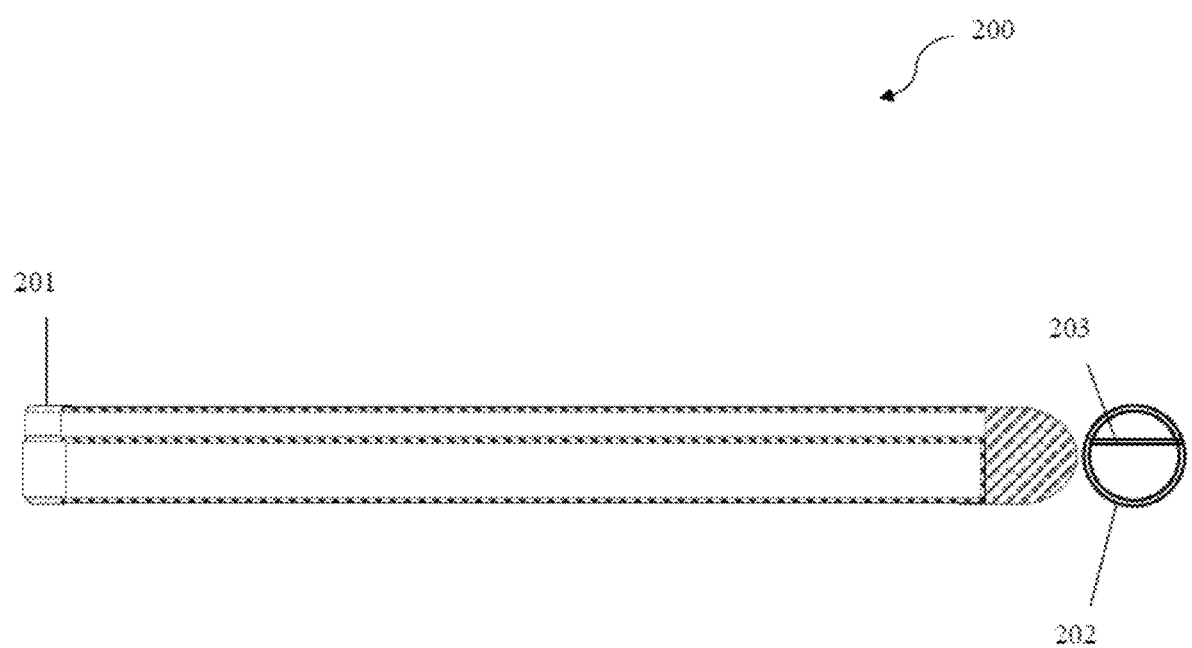
FIG. 2 illustrates, a cross-sectional view 200 of the digital device 100 facilitating body cavity screening and diagnosis.

Referring now to FIG. 2, a cross-sectional view 200 of the digital device 100 facilitating body cavity screening and diagnosis is illustrated in accordance to the present subject matter. In one embodiment, the casing 101 may comprise a separate cap-like fixture 201 on the backside for locking the probe 103, wherein the locking may be either screwed on with threading or clamped or any such locking mechanism. In one embodiment, the casing 101 may be additionally covered with a disposable clear plastic sheath that does not cover the transparent cap 105 wherein the transparent cap 105 may be fixed at the viewport. In one embodiment, the casing 101 may comprise an internal divider and threads on both ends of the casing 101. In one embodiment, a cross section views 202, 203 of the casing 101 and divider is shown in FIG. 2.

Figure 3:
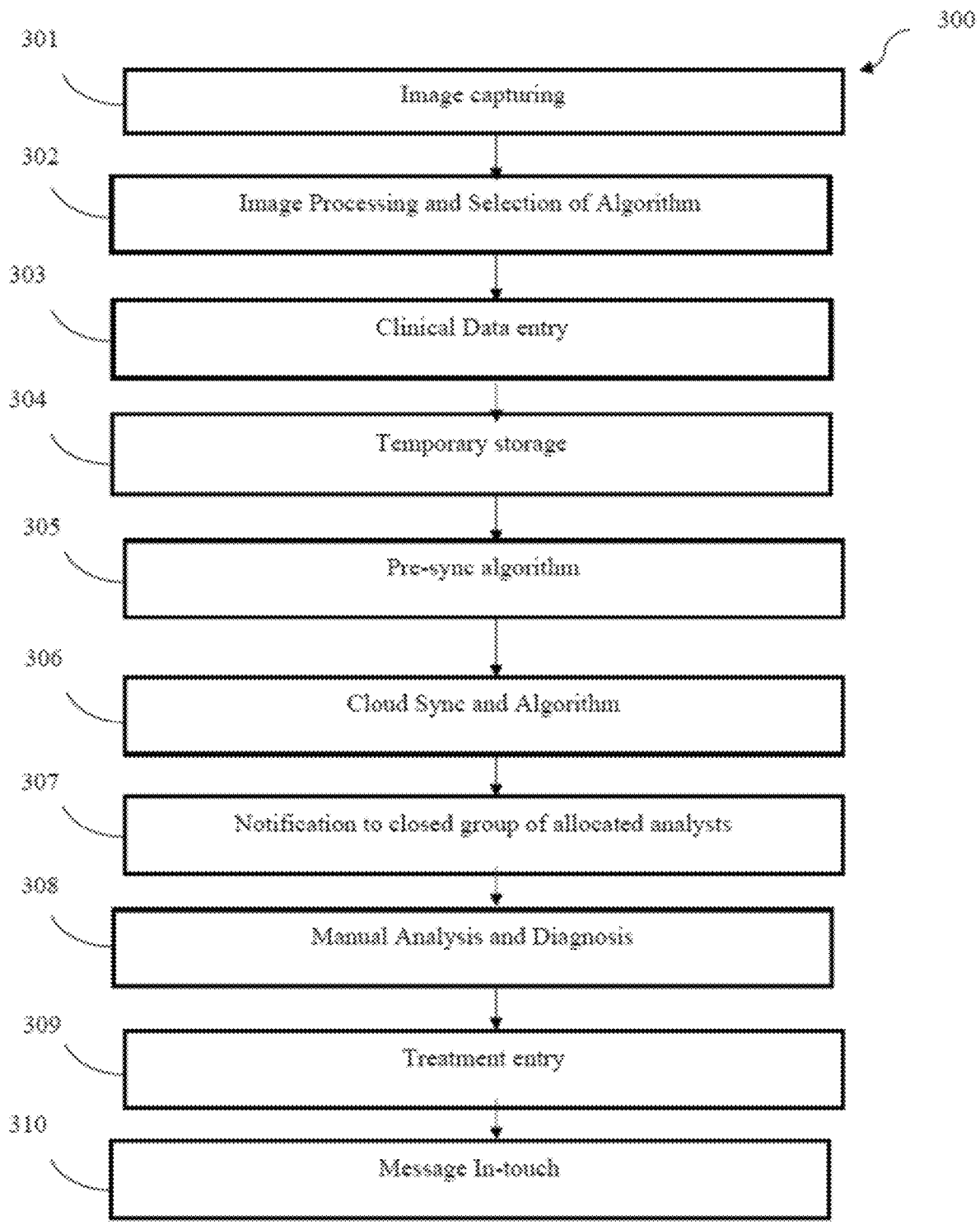
FIG. 3 illustrates, a flowchart of method 300 facilitating screening and diagnosis of the body cavity.

Referring now to FIG. 3, a flowchart of method 300 facilitating screening and diagnosis of the body cavity is illustrated in accordance with the present subject matter. At step 301, the image may be captured. In one embodiment, image of the abnormalities in the body cavity may be captured via image capturing means 106.

At step 302, image processing and selection of algorithm may be performed. Said step 302 may comprise feature selection wherein dominant features in each data set that represents the input e.g., actual image vs. histopathology vs. cytopathology etc may be performed. Since, the device 100 uses actual image data, digital image processing may be performed to build the data set. The image processing, in one embodiment, may comprise noise removal, registration, segmentation of tissue types, removal of pixels with blood and reflection. Further, image processing may further comprise, application of colour filters. Further, data extraction using specific techniques for each feature may be performed. In one embodiment, the images may be processed using at least one machine learning technique selected from a group comprising clustering algorithms such as K-Means Clustering, classification algorithms such as K-Nearest Neighbors Classification, Two-Class Decision Jungle Classification, Markov Random Field Classification, Multi-class Neural Network Classification and Anomaly Detection.

At step 303, clinical data entry may be performed. In one embodiment, the clinical data may be entered in the computing device, as per requirement, wherein the clinical data may comprise of relevant details such as patient demographics and family health background, behavioural patterns that may present suspect causes of this type of abnormality, other information such as observation of any other symptoms in the patient, prior health history such as ailments and treatments if any as well as other health history relevant to the examination at hand such as parity-gravida in case of cervical cancer, specific health parameters such as vitals and any other parameters related to the examination at hand.

Further, at step 304, temporary storage may be done. The clinical data entered at step 303 may be temporary stored in the computing device.

At step 305, a pre-sync algorithm may be executed. A pre-sync algorithm may be optionally used in case the data for synchronization is large or as per the requirement of processing.

At step 306, cloud sync and algorithm may be performed. Said cloud syncing and algorithm also may be optional and depending on the data entered and requirement of the processing.

At step 307, a notification may be given to a closed group of allocated analysts. In one embodiment, said notification may comprise a simple lead-in text message that leads to the examination record entered by the probe user i.e., the healthcare professional who is on site of the examination. The notification may be transmitted via local or wireless communication perhaps using standard mobile notification protocols available in the market.

At step 308, manual analysis and diagnosis may be performed. Based on the notification received, manual analysis and diagnosis of the received data may be performed.

At step 309, treatment entry may be done. In one embodiment, after the analysis and diagnosis, a suitable treatment may be suggested or entered in the computing device.

At step 310, stipulated message may be received. In one embodiment, the message may comprise the details regarding the treatment necessary for curing the abnormalities in the body cavity of the patient.

The processor of the computing device may perform the above mentioned steps.

In a preferred embodiment, the digital device 100 facilitating body cavity screening and diagnosis may comprise a casing 101 with dimensions 14 mm external diameter and 200 mm length, a USB camera probe 103 with dimensions 7 mm external diameter and 200 mm minimum cable length with 3 white and 3 green LEDs and having CMOS sensor with 2MP image resolution and 640×480 fps rate, a spray tube 102 with dimensions 3 mm external diameter and 2 mm internal diameter, an outer cuff 104 with dimensions 14 mm inner diameter and 40 mm outer diameter when inflated, a pressure pump tube 108 with dimensions 3 mm external diameter and 2 mm internal diameter. In one preferred embodiment, the digital device 100 may be used in visual inspection of orifices such as vagina and cervix of female mammals, and anus of all mammals, and mouth/throat for any purpose. The digital device 100 may be used without a speculum preferably to provide a surround-view that can be captured on a computing device so that the data may be put through a machine learning system to provide a guidance to the healthcare providers responsible for screening. The digital device 100 may be connected to this data should be able to link a follow-up care regime for a true positive patient appropriate to the type(s) of abnormalities that were detected. The digital device 100 may be effectively used in screening and detection of many conditions which may be visually indicative including polyps, cysts (Nabothian follicles), stenosed cervix (narrower opening), warts, and lesions representing squamous or glandular pre-cancer or cancer, etc. The digital device 100 may have the ability to inflate the vagina using an outer cuff 104, ability to provide a view of the vaginal walls, a modular structure giving the freedom to use any miniature camera 103 (or 106 as given in front view) or any computing device with the casing 101, additional channels 102 to use instruments, ability to apply liquid agents such as acetic acid and Lugol's Iodine using an external refillable pump or spray canister, a clear viewport at the distal end of the casing 101, a tampon-like size and shape aimed at easy insertion, ability to sterilize the casing 101 through autoclave or cidex, and ability to interpret the results using a computer implemented module that has Artificial Intelligence.

Figure 4:
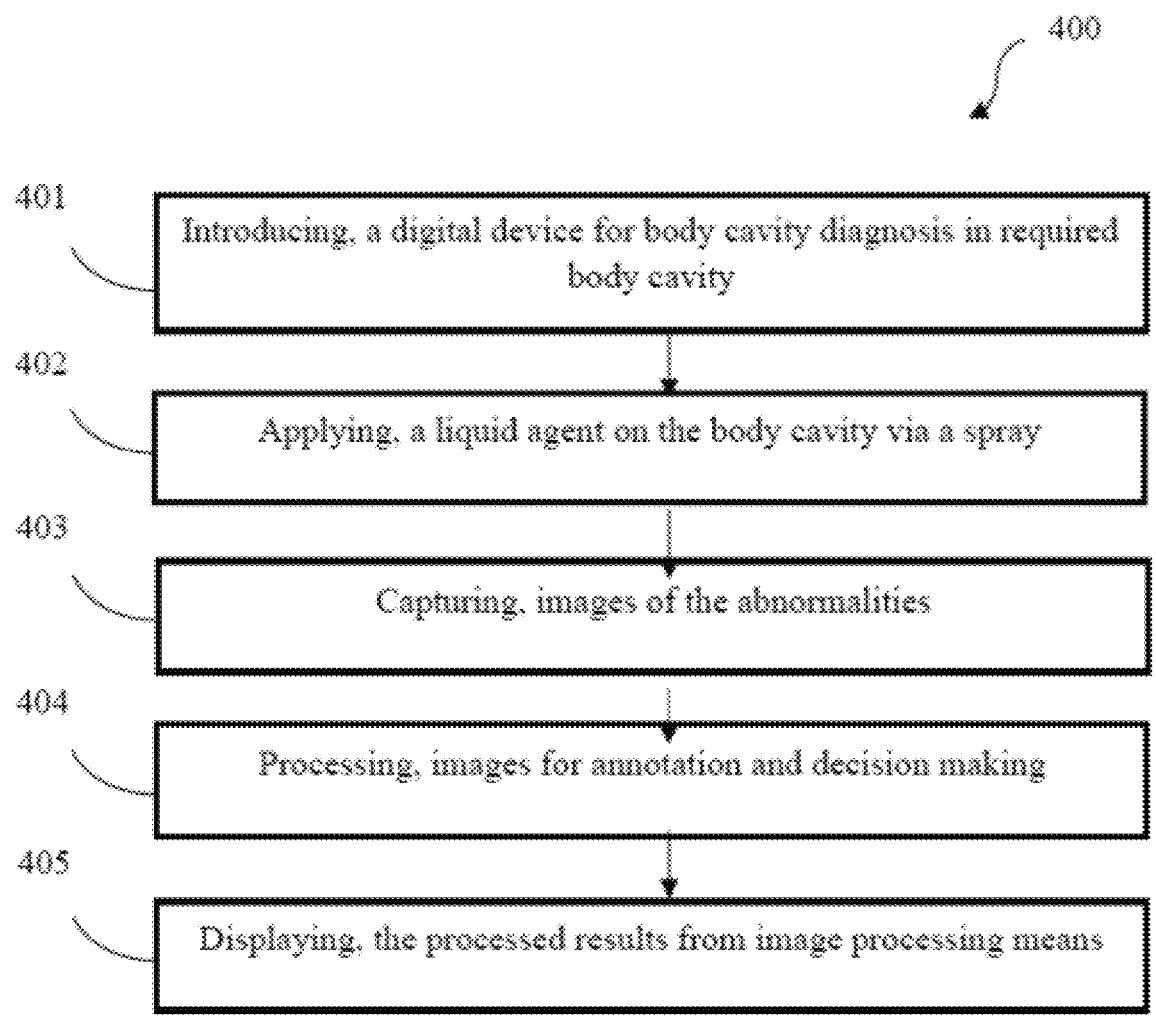
FIG. 4 illustrates, a flowchart of method 400 of use of the digital device facilitating body cavity screening and diagnosis.

Referring now to FIG. 4, a flowchart of method 400 of use of the digital device 100 facilitating body cavity screening and diagnosis is illustrated in accordance with the present subject matter. The method 400 may be characterized in enabling the body cavity diagnosis without using a speculum. At step 401, the digital device 100 for body cavity diagnosis may be introduced or inserted in the required body cavity.

At step 402, the liquid agent may be applied on the body cavity. In one embodiment, acetic acid or Lugol's iodine may be applied via a spray on the body cavity for visualization of abnormalities. The spray may be connected via a straw/tube 109 to a pressure canister external to the body cavity.

At step 403, capturing of images of the abnormalities may be performed. In one embodiment, the image capturing means 106 may be configured to capture the images of the abnormalities in the body cavity.

At step 404, processing of images may be performed. In one embodiment, image processing means may process images of the abnormalities for annotation and decision making.

At step 405, displaying of processed results may be performed. In one embodiment, the processed results from the image processing means may be displayed via wireless remote communication components such as, but may not be limited to mobile phones, computer, laptops and like devices.

The method 400 may provide visual guidance for conducting inspection, cleaning, tissue collection, biopsies and medicine application.

The digital device 100 facilitating body cavity screening and diagnosis may be used for orifices and other internal surgeries. The digital device 100 enables identifying the specific abnormalities present in a body cavity or orifice and refer them for further review and link to a follow up care plan. The digital device 100 may be able to inspect the female vagina and cervix without causing specular reflection and discomfort to patient. Further the device 100 may provide an affordable screening probe for body orifices. In one embodiment, the digital device 100 may be configured to closely view the female vagina and cervix without using a speculum while performing a procedure. In another embodiment, the digital device 100 may provide visually guided access to the cervical os for any procedure such as advancing a catheter while viewing the nearby area clearly. In yet another embodiment, the digital device 100 may be configured to closely view the female vagina and cervix without using a speculum and without a specific body position such as supine, dorsal recumbent, or lithotomy. The digital device 100 may be configured to provide a modular screening probe, with replaceable camera, replaceable computing device, and disposable cuff, for visual inspection of body cavities and orifices. Further, the digital device 100 may be able to perform VIA/VIAM/VILI easily without removing and reinserting probe again and again, while not using a speculum, for detection of cervical pre-cancer and cancer easily with help of whitened or colored tissue. The device 100 may also be able to provide one-step single-visit diagnostic confirmation of any cervical abnormality for uptake of a "screen and treat" program by avoiding a separate diagnostic colposcopy usually needed after VIA/VILI. In one embodiment, the digital device 100 may be configured to reduce or remove subjectivity from the conclusion of a visual inspection of any body cavity or orifice by utilizing intelligence gathered from an Artificially Intelligent system. Said device 100 may reduce or remove subjectivity from the conclusion of a visual inspection of any body cavity or orifice by consulting expert(s) who may be remote to the site of the examination. The digital device 100 may be able to link a follow-up care program appropriate for the identified abnormality and track it through a software system, preferably cloud-enabled and mobile-connected. Examples of people who could be involved in such a care program for a given patient could be: One or more from the list—the treating doctor, the consulting expert, the patient, the family or caregiver of patient, an NGO staff member, a government official, lab personnel, a pharmacist, a research scholar, etc. to enable self-examination of certain body orifices e.g., mouth, vagina, anus, for wellness and regular at-home care. The digital device 100 may also be configured to enable a guided application of specific topical creams and ointments or anesthetics in certain body orifices using special tube-and-squeezer or similar attachments, while visualizing the area on a connected mobile or computing device. The application may be done in a clinical setup or by self at home. The digital device 100 connected with a computing device may enable objective documentation of inspected area, with guidance for measuring specific features noted during the examination. The guidance can be in the form of virtual or on-screen cross-hair view or ruler or grid on the connected computing device.

Although implementations of a digital device 100 facilitating body cavity diagnosis have been described in language specific to structural features and/or methods, it is to be understood that the appended claims are not necessarily limited to the specific features or methods described. Rather, the specific features are disclosed as examples of a digital device 100 facilitating body cavity diagnosis.

We claim:

1. A digital device (100) for facilitating body cavity screening and diagnosis, wherein the digital device (100) is characterized in enabling the body cavity screening and diagnosis without using a speculum, wherein the digital device (100) comprising:
- a probe (103) configured for optical and digital screening and diagnosis of abnormalities in body cavities, wherein the probe (103) is connected to local and wireless remote communication components for displaying one or more captured images, wherein the probe (103) comprises
- an in-situ image capturing means (106) with a light source for capturing images of the abnormalities,
- a processor coupled to a computing device for digital image diagnosis, and
- one or more angulation wires (107) for providing angulation control to the image capturing means (106), wherein the one or more angulation wires (107) are controlled by a pulley or a chain-sprocket mechanism with stoppers to limit the articulation and external knobs to control the turning in required direction; and
- a casing (101) enclosing the probe (103) and capable of being separated from the probe (103), wherein the casing (101) comprises
- a separate channel comprising a tube (109) for carrying and further spraying a liquid agent comprising acetic acid and Lugol's iodine,
- an additional channel (102) configured to carry a plurality of instruments comprising a spatula for scraping of cells, a cytobrush to collect scraped cells, a swab for cleaning, forceps to lift the walls of the casing, a grasping device and pair of scissors to remove tissues,
- a transparent cap (105) having a hole that aligns with the additional channel (102) and is configured for visualizing walls and structure of the cavity, and
- an expandable outer cuff (104) made of a rubber or plastic material which is placed on an exterior of the casing (101) and is configured for separating walls of a body part, wherein the expandable outer cuff comprises a polymer gel powder, and wherein the expandable outer cuff (104) is configured to be introduced into the body cavity in a deflated position and subsequently inflated using a liquid injected into the expandable outer cuff causing the polymer gel powder to bloat into a gel.

2. The digital device (100) for facilitating body cavity screening and diagnosis as claimed in claim 1 wherein, diameter of the probe (103) is up to 15 mm.

3. The digital device (100) for facilitating body cavity screening and diagnosis as claimed in claim 1 wherein, diameter of the casing (101) is up to 20 mm and is disposable or sterilisable or an autoclavable sheath.

4. The digital device (100) for facilitating body cavity screening and diagnosis as claimed in claim 3 wherein, the casing (101) is either of a stainless steel, a rubber, or a plastic, wherein the stainless steel facilitates autoclaving and the plastic facilitates disposability.

5. The digital device (100) for facilitating body cavity screening and diagnosis as claimed in claim 1 wherein, the image capturing means (106) comprises of a camera with specifications comprising at least 2-5 megapixel resolution, a lens diameter of up to 7.5 mm, and a resolution of at least 640*480.

6. The digital device (100) for facilitating body cavity screening and diagnosis as claimed in claim 5 wherein, said image capturing means (106) is a UV-light camera with sensors providing fluorescence information to the computing device or a fiberscope or a rigid endoscope with a rod lens system without a sheath.

7. The digital device (100) for facilitating body cavity screening and diagnosis as claimed in claim 6 wherein, said image capturing means (106) comprises:
- a flexi-tip CMOS or CCD-Chip with the lens diameter to provide an image of at least 3 mm distance from the body cavity being viewed or
- a distal tip, wherein the distal tip is fit with one or more foroblique mirror tips of angular fits selected from 30°, 60°, and 75° or the distal tip has the one or more angulation wires (107) adjacent to the distal tip.

8. The digital device (100) for facilitating body cavity screening and diagnosis as claimed in claim 1 wherein, the one or more angulation wires (107) have a dimension of up to 5 mm diameter.

9. The digital device (100) for facilitating body cavity screening and diagnosis as claimed in claim 8 wherein, said local and wireless remote communication enables connectivity between a remote consultation and a machine learning algorithm of the computing device.

10. The digital device (100) for facilitating body cavity screening and diagnosis as claimed in claim 1 wherein, the transparent cap (105) on a lens side of the probe (103) has a rounded shape to allow insertion into the body cavity and is hollow on an inner side to allow movement of head of the probe (103) encased within and has the hole that aligns with the additional channel (102) of the casing (101) to allow outlet for the instruments as well as sprays, wherein said transparent cap (105) is made of a clear, transparent polycarbonate or any material that provides full transparency and has a non-reflective surface, wherein the transparent cap (105) is screw-fitted onto the casing (101) by using threading or glue for disposable use in which case the transparent cap will be of a material that does not degrade with contact of sterilization chemicals suitable to kill microbes in that particular infected body organ.

11. The digital device (100) for facilitating body cavity screening and diagnosis as claimed in claim 1 wherein, the local and wireless remote communication components comprise either a mobile phone, a computer or a laptop, via USB, BLE or WiFi.

12. The digital device (100) for facilitating body cavity screening and diagnosis as claimed in claim 1 wherein, said computing device comprise logic that enables linkage of care plans and captured images and videos of the body cavities captured by the image capturing means (106) of said device (100).

13. The digital device (100) for facilitating body cavity screening and diagnosis as claimed in claim 1 wherein, the probe (103) is capable of providing stereoscopic vision for the visualization of abnormalities in the body cavities.

14. The digital device (100) for facilitating body cavity screening and diagnosis as claimed in claim 1 wherein, said digital device (100) for body cavity screening and diagnosis is used for orifices and other internal surgeries.

* * * * *